United States Patent [19]

Schole

[11] 4,367,219

[45] Jan. 4, 1983

[54] FLUORIDE CONTAINING DENTIFRICE

[76] Inventor: Murray L. Schole, 487 Munroe Ave., North Tarrytown, N.Y. 10591

[21] Appl. No.: 324,875

[22] Filed: Nov. 25, 1981

[51] Int. Cl.$^3$ ............................ A61K 7/18; A61K 7/24
[52] U.S. Cl. ......................................... 424/52; 424/49; 424/54; 424/55
[58] Field of Search ....................................... 424/49–58

[56] References Cited

U.S. PATENT DOCUMENTS

| | | | |
|---|---|---|---|
| Re. 30,675 | 7/1981 | Schole | 424/54 |
| 1,633,336 | 6/1927 | Larson | 424/49 |
| 1,936,456 | 11/1933 | Larson et al. | 424/55 |
| 3,004,897 | 10/1961 | Shore | 424/54 |
| 3,122,483 | 2/1964 | Rosenthal | 424/55 |
| 3,699,221 | 10/1972 | Schole et al. | 424/54 |
| 3,988,434 | 10/1976 | Schole et al. | 424/54 |
| 4,130,638 | 12/1978 | Dhabhar et al. | 424/55 |
| 4,175,120 | 11/1979 | Schole | 424/54 |
| 4,283,385 | 8/1981 | Dhabhar et al. | 424/52 |

FOREIGN PATENT DOCUMENTS 680108 2/1964 Canada .
907514 8/1972 Canada .

*Primary Examiner*—Shep K. Rose
*Attorney, Agent, or Firm*—Brooks, Haidt, Haffner & Delahunty

[57] ABSTRACT

A water-containing dentifrice having increased fluoride up-take and enhanced anti-caries effect is provided utilizing a combination of strontium edetate, alkali metal ricinoleate and soluble fluoride.

6 Claims, No Drawings

FLUORIDE CONTAINING DENTIFRICE

This invention relates to water-containing dentifrices containing fluoride and in particular provides a dentifrice having improved fluoride up-take.

The inclusion of fluoride ion in dentifrices, such as toothpaste, has been long known to have an anti-caries activity. the shelf-life of fluoride containing dentifrices, such as toothpaste, has been poor, as has been evidenced by loss of the fluoride level over a period of time, as much as 28% in six months. It is believed this loss in availability is a result of the formation of insoluble fluoride salts, as by reaction of fluoride ion with calcium present in bulk excipients, i.e., abrasives such as calcium carbonate, calcium phosphate and insoluble metaphosphates. As a result the fluoride ion is slowly removed in insoluble form and thus becomes unavailable to react with the calcium hydroxyapatite of the tooth.

It has been known for some time that chelating agents, such as salts of ethylenediamine tetraacetic acid, for example, tetrasodium edetate and strontium disodium edetate, sequester calcium ions such that the formation of insoluble fluoride salts is inhibited, and the shelf-life of fluoride dentifrices is enhanced. Strontium disodium edetate itself in dentifrices has valuable therapeutic properties in treating hypersensitive dentine, reducing gingivitis and the like. Moreover, it has been found that when strontium edetate is combined in a dentifrice with soluble ricinoleates, such as sodium ricinoleate, the combination has a beneficial effect of inhibiting plaque formation.

It has now been found, in accordance with this invention, that the combination of fluoride ion in a dentifrice containing strontium edetate and a water-soluble ricinoleate compound results in a surprising increase in fluoride up-take, and the anti caries effect of the fluoride ion is enhanced by the combination.

In accordance with this invention the fluoride ion is preferably supplied by alkali metal fluoride, such as sodium fluoride, although other water-soluble fluorides such as the various monofluorophosphates (MFP) of alkali metals and ammonia are also suitable. Stannous fluoride, cupric fluoride and other water-soluble fluorides which might otherwise be used to supply fluoride ion in dentifrices are not suitable in accordance with the present invention because the cation is sequestered by the chelate and interferes with its action. Preferably the amount of fluoride is in the weight range, calculated as fluoride ion, of 0.02% to 2.0 wt. percent, preferably from about 0.05% to about 0.5% by weight.

In accordance with the invention strontium edetate should be present in the dentifrice in an amount up to 25 wt. percent, calculated as strontium disodium edetate, but smaller amounts, as low as 1.0 wt. percent may be effective. The strontium edetate can be formed in advance as the disodium or other alkali metal salt, or it can be prepared in situ in the dentifrice as a mixture of a water soluble salt of edetic acid (EDTA) together with a pharmacologically innocuous water-soluble strontium salt preferably in equivalent amounts such that the pH remains neutral.

The ricinoleate can be any of the alkali metal salts of ricinoleic acid (d-12-hydroxy-cis-9-octadecenoic acid), but preferably is the sodium salt. The amount of the ricinoleate is not particularly critical and can be as high as 10 wt. percent, calculated as the sodium salt, although amounts as low as 0.1 wt. percent are also effective.

Generally the dentrifice is formulated in a conventional manner, other than for the inclusion of the above noted ingredients, with humectants, flavoring agents, coloring agents, sweetners, etc., as desired. The amount of surface active agent required is reduced by the presence of the ricinoleate and can be entirely supplanted by the ricinoleate.

The dentifrices of the present invention are water-based systems, and strontium edetate is soluble in the dentifrice. Consequently cations having pKa with edetic acid greater than that of strontium are to be avoided. Thus calcium carbonate, calcium phosphate and the like which conventially are used as bulk excipients can not be used in this dentifrice. In their place strontium carbonate or the like can be used, or silica gels can be employed as abrasives (see U.S. Pat. Nos. 3,538,230 and 4,153,680). Thus, the dentifrice of the invention should not include any water insoluble calcium, magnesium or aluminum compounds, such as those which ordinarily might be incorporated as adjuvents and bulk excipients. Similarly, as noted above fluoride ion sources such as stannous fluoride can not be used.

The following are examples of several dentifrices in accordance with this invention.

EXAMPLE I

A tooth paste is prepared by slowly adding strontium carbonate to an equivalent amount of disodium edetate (disodium salt of ethylene diamine tetraacetic acid) in aqueous solution at a temperature of 70°–80°. After completion of the reqction (evolution of $CO_2$ gas ceases) the pH is adjusted to 7 or 8 by addition of HCl, and water is added to reduce the resultant strontium edetate content (calculated as the disodium salt) to 25 weight percent. Insoluble metaphosphate (IMP) is then added followed by other ingredients according to the following formulation.:

|  | gms |
| --- | --- |
| Strontium edetate calculated as the disodium salt | 5.0 |
| IMP | 32.0 |
| Sorbitol (70% aqueous solution) | 17.0 |
| Sodium ricinoleate | 1.2 |
| Sodium lauryl sulfate | 1.0 |
| Sodium CMC (12μ) | 1.5 |
| Cabosil | 1.2 |
| Sodium fluoride | 0.22 |
| Xanthan gum | 0.7 |
| Sodium saccharin | 0.45 |
| Methylparaben | 0.06 |
| Propyl paraben | 0.02 |
| Flavoring | 1.05 |
| Water QSAD to 100 gms | |

In a normal program of regular dental care this formulation even after extended storage, not only inhibits the formation of plaque and build-up of calculus but enhances fluoride up-take to minimize development of caries.

EXAMPLE II

Another toothpaste in accordance with the invention is formulated following the procedure of Example I using MFP (sodium monofluorophosphate) in place of sodium fluoride as follows:

| | | |
|---|---|---|
| Strontium edetate | 1.25 | parts by weight |
| IMP | 32 | parts by weight |
| Sorbitol (70% solution) | 17 | parts by weight |
| Glycerine | 8 | parts by weight |
| Sodium ricinoleate | 0.9 | parts by weight |
| Sodium lauryl sulfate | 0.9 | parts by weight |
| Sodium cmc | 1.65 | parts by weight |
| Cabosil | 1.2 | parts by weight |
| MFP | 0.76 | parts by weight |
| Xanthan gum | 0.5 | parts by weight |
| Sodium saccharin | 0.45 | parts by weight |
| Methylparaben | 0.06 | parts by weight |
| Propyl paraben | 0.02 | parts by weight |
| Methyl salicylate | 0.40 | parts by weight |
| Peppermint Oil | 0.1 | parts by weight |
| $H_2O$ qsad to | 100 | parts by weight |

EXAMPLES III–V

Toothpastes in accordance with this invention using hydrous silica gel as abrasive are formulated as follows:

EXAMPLE III–V

| Example No. | III | IV | V | |
|---|---|---|---|---|
| Strontium edetate | 2.5 | 5.0 | 12.5 | parts by weight |
| Sodium ricinoleate | 0.5 | 1.0 | 2 | parts by weight |
| Sodium fluoride | 0.1 | 0.22 | 0.8 | parts by weight |
| Sorbitol (70% solution) | 21.0 | 21.0 | 21.0 | parts by weight |
| Hydrous silica gel (24% T.V) | 28.5 | 28.5 | 28.5 | parts by weight |
| Glycerine | 7.24 | 7.24 | 7.24 | parts by weight |
| Sodium lauryl sulfate | 2.5 | 2.0 | 1.0 | parts by weight |
| Cabosil | .55 | .55 | .55 | parts by weight |
| Sodium saccharin | .45 | .45 | .45 | parts by weight |
| Keltrol F | .4 | .4 | .4 | parts by weight |
| Methylparaben | .06 | .06 | .06 | parts by weight |
| Propyl paraben | .02 | .02 | .02 | parts by weight |
| Peppermint oil | .86 | .86 | .86 | parts by weight |
| Menthol | .34 | .34 | .34 | parts by weight |
| Clove oil | .06 | .06 | .06 | parts by weight |
| Anathol | .05 | .05 | .05 | parts by weight |
| Spearmint oil | .49 | .49 | .49 | parts by weight |
| Vanillin | .003 | .003 | .003 | parts by weight |
| Leaf alcohol | .004 | .004 | .004 | parts by weight |
| Water QSAD to 100 parts by weight. | | | | |

EXAMPLE VI

A preferred toothpaste in accordance with this invention has the following formulation:

| | | |
|---|---|---|
| Strontium edetate | 5.0 | parts by weight |
| Sodium ricinoleate | 0.5 | parts by weight |
| Sodium fluoride | 0.22 | parts by weight |
| Strontium carbonate | 25.0 | parts by weight |
| Cetyl pyridinium chloride | 0.5 | parts by weight |
| Oil of cassia | 0.75 | parts by weight |
| Oil of wintergreen | 1.0 | parts by weight |
| Propylene glycol | 25.0 | parts by weight |
| Natrosol | 1.7 | parts by weight |
| Sodium saccharin | 1.2 | parts by weight |
| Water QSAD to | 100 | parts by weight |

I claim:
1. A water-containing dentifrice consisting essentially of strontium edetate in an amount of about 1.0 wt. percent to about 25 wt. percent, an alkali metal salt of ricinoleic acid in an amount of about 0.1 wt. percent to about 10 wt. percent and a source of fluoride ion providing a fluoride concentration in the dentifrice from about 0.02 wt. percent to about 2.0 wt. percent.
2. A dentifrice according to claim 1 in which the ricinoleate is sodium ricinoleate.
3. A dentifrice according to claim 1 or claim 2 further comprising an abrasive.
4. A dentifrice according to claim 3 in which said abrasive is silica gel.
5. A dentifrice according to claim 3 in which said abrasive is strontium carbonate.
6. A dentifrice according to claim 3 in which said abrasive is insoluble metaphosphate.

* * * * *